United States Patent
Taylor et al.

[11] Patent Number: 5,817,984
[45] Date of Patent: Oct. 6, 1998

[54] IMPLANTABLE MEDICAL DEVICE WTIH MULTI-PIN FEEDTHROUGH

[76] Inventors: William J. Taylor, 106 Yoho Dr., Anoka, Minn. 55303; Lynn M Seifried, 5015 Luverne Ave., Minneapolis, Minn. 55419; Douglas Weiss, 11425 - 39th Ave. No., Plymouth, Minn. 55441; Joseph F. Lessar, 3742 - 114th La. NW., Coon Rapids, Minn. 55433

[21] Appl. No.: 508,811

[22] Filed: Jul. 28, 1995

[51] Int. Cl.$^6$ ....................................... H01B 17/30
[52] U.S. Cl. ..................... 174/152 GM; 501/67; 607/37
[58] Field of Search ................ 174/152 GM, 50.61; 403/272; 501/67; 607/36, 37

[56] References Cited

U.S. PATENT DOCUMENTS

| | | | |
|---|---|---|---|
| Re. 33,170 | 2/1990 | Byers | 124/419 R |
| 4,029,897 | 6/1977 | Mayer et al. | 174/152 GM |
| 4,180,700 | 12/1979 | Kraska | 174/152 GM |
| 4,217,137 | 8/1980 | Kraska | 75/165 |
| 4,220,814 | 9/1980 | Kyle et al. | 174/152 GM |
| 4,225,262 | 9/1980 | Koop | 403/272 |
| 4,349,635 | 9/1982 | Davis et al. | 174/50.61 X |
| 4,417,913 | 11/1983 | Davis et al. | 174/50.61 X |
| 4,495,917 | 1/1985 | Byers | 67/57 |
| 4,516,820 | 5/1985 | Kuzma | 439/289 |
| 4,525,766 | 6/1985 | Peterson | 361/283 |
| 4,678,868 | 7/1987 | Kraska | 174/152 GM |
| 4,730,389 | 3/1988 | Baudino et al. | 29/825 |
| 4,816,621 | 3/1989 | Huebner et al. | 174/152 GM |
| 4,874,910 | 10/1989 | McCoy | 174/152 GM |
| 4,940,858 | 7/1990 | Taylor et al. | 174/152 GM |
| 4,951,011 | 8/1990 | Heckaman | 333/33 |
| 4,991,582 | 2/1991 | Byers et al. | 607/2 |
| 5,012,807 | 5/1991 | Stutz | 128/419 P |
| 5,046,242 | 9/1991 | Kuzma | 174/152 GM X |
| 5,076,270 | 12/1991 | Stutz | 128/419 P |
| 5,103,818 | 4/1992 | Maston et al. | 607/9 |
| 5,104,755 | 4/1992 | Taylor et al. | 174/50.61 X |
| 5,250,845 | 10/1993 | Runyan | 257/729 |
| 5,294,241 | 3/1994 | Taylor | 65/59.31 |
| 5,306,581 | 4/1994 | Taylor et al. | 429/181 |
| 5,333,095 | 7/1994 | Stevenson et al. | 361/302 |
| 5,406,444 | 4/1995 | Selfried et al. | 174/152 GM X |
| 5,434,017 | 7/1995 | Berkowitz | 429/94 |
| 5,531,003 | 7/1996 | Selfried et al. | 29/25.42 |

OTHER PUBLICATIONS

"Development of Hermetic Microminiature Connectors", M.K. Neilsen, et al, Journal Of Electronic Packaging, Dec. 1991, vol. 113, p. 405.

*Primary Examiner*—Hyung S. Sough
*Attorney, Agent, or Firm*—Thomas F. Woods; Harold R. Patton

[57] ABSTRACT

A hermetically sealed implantable medical device is provided with a multi-pin arrangement including selected glass to metal or ceramic to metal seals for a feedthrough of the compression seal or matched seal type.

14 Claims, 4 Drawing Sheets

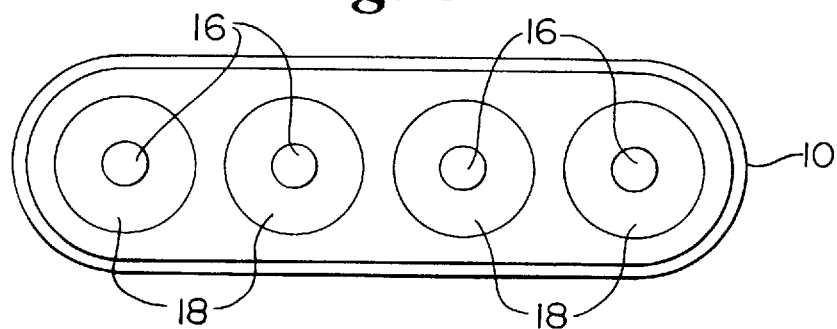
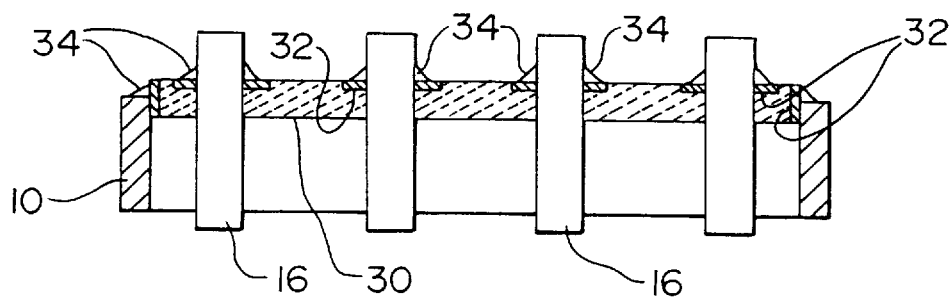

IMPLANTABLE MEDICAL DEVICE WTIH MULTI-PIN FEEDTHROUGH

FIELD OF THE INVENTION

This invention relates to electrical feedthrough devices and particularly to multiple read electrical feedthroughs for providing electrical communication with the interior of a hermetically sealed implantable medical device.

BACKGROUND OF THE INVENTION

There are numerous applications where it is necessary to penetrate a sealed container with a plurality of electrical leads so as to provide electrical access to and from electrical components enclosed within. One such application for which the present invention has particular but not limited utility is in body implantable pulse generators (e.g. for treatment of bradycardia, tachyarythmia or for muscle or nerve stimulation), referred to generally as implantable pulse generators (IPG's). The heart pacemaker is a well known example of one type of IPG. Typical devices of this type are formed of a metal container housing the electrical and power source components of the IPG with a lid or the like welded to the container to close the device and provide it with a hermetic seal. An electrical lead is electrically connected to the IPG by means of attachment to one or more feedthroughs which penetrate the container but maintain the hermetically sealed environment thereof. A typical feedthrough consists of an external metal part (a frame or ferrule) into which preformed solid or sintered glass part is sealed. Within the glass part, one or more metal leads (pins) are sealed. Since the reliability of critical implantable medical devices depend on hermetic sealing of various components, the integrity of the glass to metal seals used in battery components and the seal between the internal electrical components and the human body is of paramount importance.

In many implantable medical devices, metals which have long term corrosion resistance and biocompatibility are needed to provide years of reliable service since maintenance or repair possibilities for the devices are extremely limited. Moreover, since such devices are sometimes life-saving for the patient, failures of the feedthrough materials can have catastrophic consequences. Therefore, metals like titanium, niobium, tantalum, platinum and the like are use due to their well known superior corrosion resistance and biocompatability.

As such devices have undergone development, they have become smaller yet more electronically sophisticated, making it necessary to include more and more functions into smaller and smaller containers. This translates into a need for multi-pin feedthroughs carried by small, usually slim, containers. Multi-pin arrangements of feedthrough pins have generally been suggested before. For example, in U.S. Pat. No. 4,874,910 issued to McCoy, a number of flat pins are shown traversing a hermetic glass seal in a linear array. Or, in Neilsen et al, "*Development of Hermetic Microminiature Connections*", *Journal of Elastomeric Packaging.* December 1991, Vol 113/405–409, the stresses on a compression seal for a multi-pin device are modeled. However, the successful combination of materials which include the corrosion resistance and biocompatibility required for an implantable medical device have not been disclosed.

SUMMARY OF THE INVENTION

This invention, by judicious selection and combination of component materials (ferrule, seal insulator and pin) provides for either compression or match seals for electrical feedthroughs, the pins of which are arranged in a multi-pin array together with corrosion resistance and biocompatability needed in an implantable medical device. The resultant feedthrough configuration accommodates at least two arranged pins and may be expanded linearly to any desired number. A linear configuration results in easy identification of the pins and facilitates automated connection therewith and maintains device slimness even when a large number of pins are included in the feedthrough arrangement. The linear arrangement also allows easy access allowing the use of a plug-in electrical connector to facilitate rapid connections to the device components.

BRIEF DESCRIPTION OF THE FIGURES

FIGS. 7 and 8 show similar views respectively of an optional ceramic disc embodiment.

FIG. 9 is a schematic showing of a metallized ceramic to metal configuration according to the invention.

DESCRIPTION OF THE PREFERRED EMBODIMENT

Figure 1:
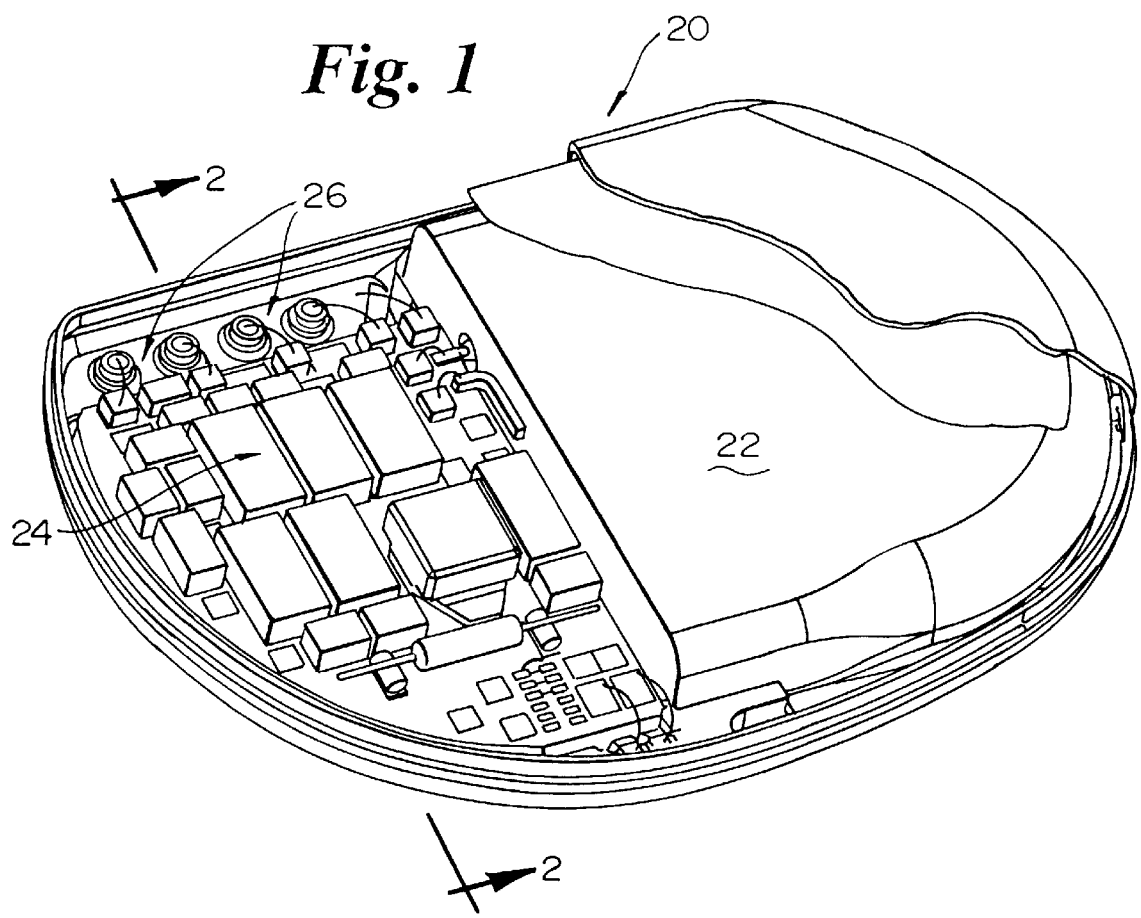
FIG. 1 is cutaway perspective view of an exemplary IPG.

While this invention may be embodied in many different forms, there are shown in the drawings and described in detail herein specific preferred embodiments as applied to IPG's. The present invention is exemplified as to its principles and is not meant to be limited to the particular embodiments illustrated.

Figure 2:
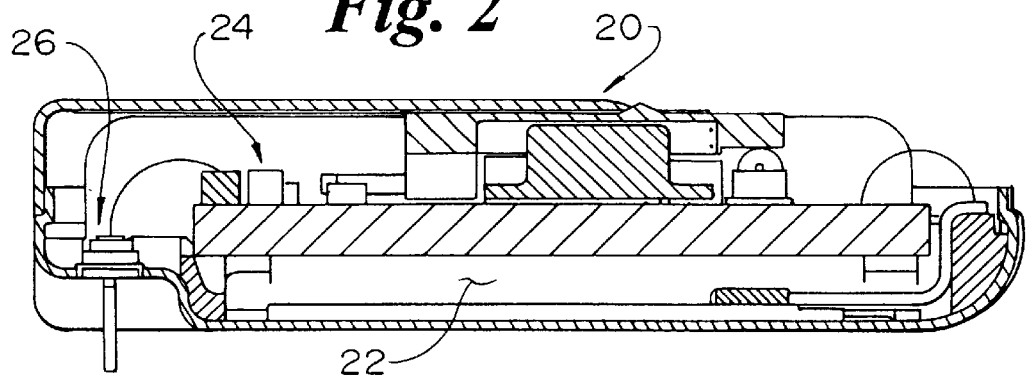
FIG. 2 rows a cross-section taken along line 2—2 in FIG. 1 of the IPG interior and feedthrough.

Referring first to FIGS. 1 and 2, an IPG 20 is shown generically. It includes a battery section 22, a circuit section 24 and a linearly arranged plurality of feedthroughs 26.

Figure 3:
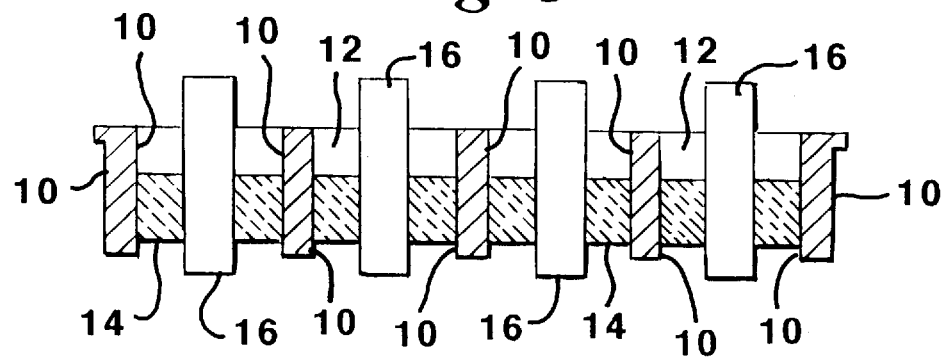
FIGS. 3 and 4 show a cross-sectional and elevational views respectively of a first configuration according to the invention (separate insulator for each pin).
Figure 4:
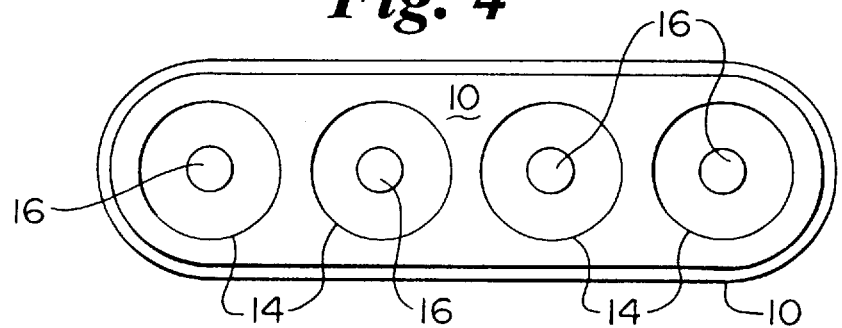

Different feedthrough configurations may be used in the device illustrated in FIGS. 1 and 2 according to this invention and welded into place as a unit in an aperature of the IPG 20. Configurations are shown in FIGS. 3–4 and 5–6. A first linear configuration is shown in FIGS. 3 and 4 having an elongated titanium ferrule 10 having a plurality of openings 12 extending therethrough. The ferrule 10 can be provided by conventional machining, stamping or chemical etching operations, etc. Each of the openings 12 receives a linear array of discrete sealing insulator bodies 14 more specifically described hereinbelow as to choice of materials and which in turn carry a linear array of pins 16 (more specifically disclosed herein below as to choice of materials) which are preferably centered in each of the openings 12.

Figure 5:
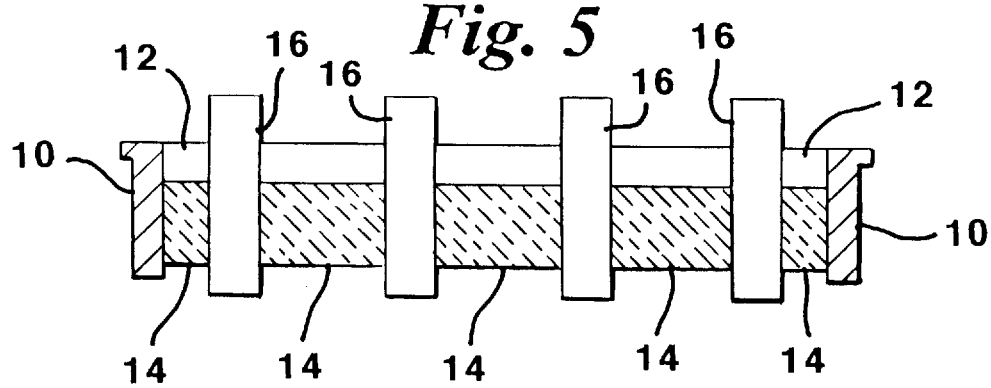
FIGS. 5 and 6 show a cross-sectional and elevational views respectively of a second configuration according to the invention (common insulator).
Figure 6:
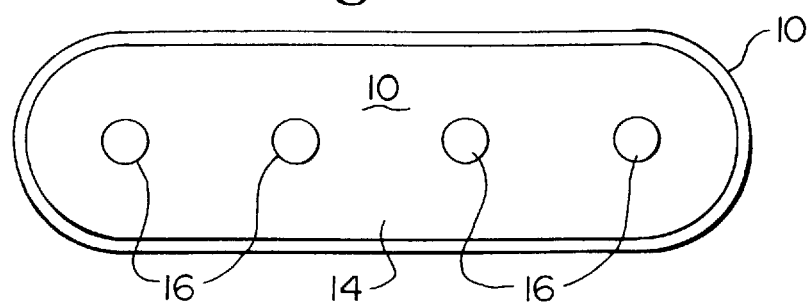

Another linear configuration is shown in FIGS. 5 and 6, also having an elongated titanium ferrule 10 having a single elongated opening 12 therethrough which receives a single elongate sealing body 14 (more specifically described herein below as to materials) and which in turn carries a linear array of pins 16 centered in the opening 12.

Figure 7:
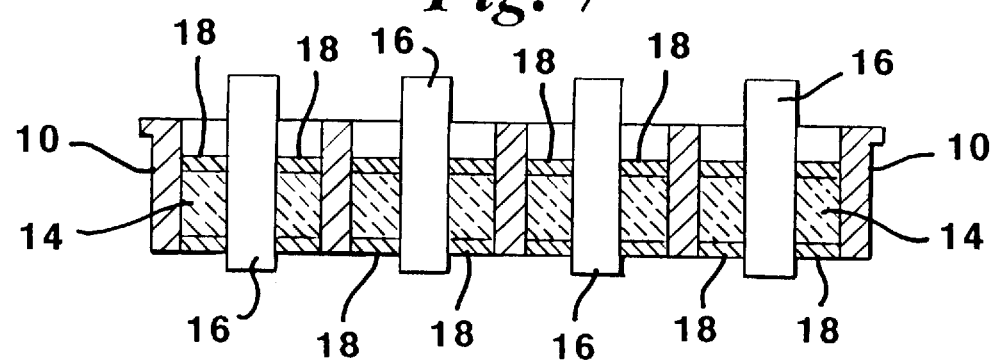

Lastly, FIGS. 7 and 8 show an embodiment similar to FIGS. 3 and 4 optionally including an array of discrete upper and/or lower ceramic discs 18 covering the insulators bodies 12 and surrounding pins 16. A similar option (not shown) may be included in the configuration of FIGS. 5 and 6 wherein a simple elongate ceramic disc is included on the upper and/or lower surfaces of the insulator body 14. One purpose of the ceramic body 18 is to provide a platform to control vertical wetting of the glass insulator body in the ferrule (housing), i.e., as the ferrule and glass are heated in a furnace, to keep the glass away from the recessed area which is also the weld zone. This will prevent cracking of the sealing glass during the welding operation later used to install the completed feedthrough in the IPG. Another purpose for the ceramic body is to position the sealing glass, housing and pin when they are heated in the furnace, thereby maintaining the proper location of the elements. Another purpose for the ceramic body is to provide a barrier layer between the sealing glass and the graphite fixturing (not shown) that supports the feedthrough materials during the sealing operation. This keeps the glass from sticking to the fixturing, a problem which may otherwise occur due to deposition of metal vapors onto the fixturing during the glass sealing operation, or the chemical reaction of the molten glass with the fixture material.

Two ceramic bodies similar to the arrangement shown in FIG. 7 may be used to provide electrical insulation with glass in between. Not all glasses deform easily at their sealing temperatures. High viscosity glasses may require mechanical deformation by weights from above. Often this "weight system" requires direct contact with the sealing glass by a non adherent material such as graphite. However, as was stated earlier, with specific glass compositions required when sealing glass to titanium, graphite may not be as non-adherent as desired. Therefore, mechanical deformation of the sealing glass may require providing a "sandwich" with the glass located between the electrically non-conductive material which do not adhere to the graphite but adhere to the glass when sealing occurs.

CHOICE OF MATERIALS

In accordance with this invention the multi-pin arrangement is carried out by the joining methods and material combinations in two particular applications: 1. Glass-to-metal seals; and 2. Ceramic-to-metal seals.

Glass-to-metal seals incorporate an outer ring or ferrule 10 comprised of a weldable grade of titanium or titanium-containing alloy as shown in FIGS. 3–8. The insulator 14 is comprised of a boro-alumino silicate or boro silicate glass with a wide range of thermal expansions to match biostable pin materials such as Tantalum, Niobium, Niobium-Titanium alloy, Platinum, Platinum alloys, Titanium and Titanium alloys. Specific combinations are shown in the Table below.

TABLE

| Glass Type | Weight % Oxide | Glass Thermal Expansion | Equivalent Expansion Pin Material |
|---|---|---|---|
| Boro-Alumino Silicate (1) | $SiO_2$ = 52.0<br>$Al_2O_3$ = 5.0<br>$B_2O_3$ = 26.0<br>ZnO = 1.0<br>$Na_2O$ = 2.5<br>$K_2O$ = 10.0<br>$TiO_2$ = 2.5<br>$ZrO_2$ = 1.0 | $6.5 \times 10^{-6}$ in/in/°C. | Tantalum |
| Pemco/Mobay IR63 (2) | $SiO_2$ = 46.7<br>$B_2O_3$ = 16.6<br>$Al_2O_3$ = 4.4<br>$ZrO_2$ = 9.9 | $7.8 \times 10^{-6}$ in/in/°C. | Niobium, Niobium/Ti alloy |

TABLE-continued

| Glass Type | Weight % Oxide | Glass Thermal Expansion | Equivalent Expansion Pin Material |
|---|---|---|---|
| Boro-Alumino Silicate (3) | $Na_2O$ = 7.5<br>$K_2O$ = 0.4<br>CaO = 14.5<br>$SiO_2$ = 5–10 (6.7 preferred)<br>$Al_2O_3$ = 20–30 (22.8 preferred)<br>$B_2O_3$ = 20–30 (23.4 preferred)<br>CaO = 12–17 (12.5 preferred)<br>BaO = 0–35 (34.5 preferred)<br>MgO = 0–12<br>SrO = 0–14 | $9.0 \times 10^{-6}$ in/in/°C. | Platinum, Titanium (or: Platinum alloys and Titanium alloys) |

Sealing of a ceramic such as $Al_2O_3$ 30 to a linear titanium or niobium/titanium ferrule or housing 10 and niobium or platinum pins 16 is shown in FIG. 9. It is accomplished in a vacuum furnace by first metallizing area 32 on the ceramic 30 and then joining metallized ceramic insulator to pin (16) and ferrule (10) by melting a metal preform such as a gold preform (34) to join the assembly. This process is typically called brazing. The metallizing 32 may be accomplished by sputtering a thin layer of metal such as Niobium (Nb) onto the surface of a ceramic such as alumina ($Al_2O_3$) in appropriate bonding locations as shown. The metallized ceramic $Al_2O_3$ 30 is then brazed to the ferrule 10 and pins 16 using gold as the braze material. It will be appreciated by those skilled in the art that other ceramics and metals can also be used to join the assembly by brazing.

Of the foregoing material combinations in linear array, glass types (1) and (2) and the ceramic type provide reliable compression seals while glass type (3) provides a reliable match seal (relative to the ferrule expansion).

This completes the description of the preferred and alternate embodiments of the invention. Those skilled in the art may recognize other equivalents to the specific embodiments described herein which equivalents are intended to be encompassed by the claims hereto.

The above Examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is as follows:

1. In an implantable medical device comprising a hermetically sealed case and a feedthrough hermetically sealed in an aperture of the case, wherein the improvement comprises:

the feedthrough comprising a ferrule of biocompatible, corrosion resistant metal and having an aperture disposed therethrough, an insulator body sealed to the ferrule within the aperture of the ferrule, and at least two pins comprising tantalum and extending through the aperture of the ferrule in sealing engagement with the insulator body, wherein the biocompatible, corrosion resistant metal of the ferrule is selected from the group consisting of titanium, titanium alloys and niobium/titanium alloys, and the insulator body comprises a glass having a nominal composition of about;
$SiO_2$=52.0 wt %
$Al_2O_3$=5.0 wt %
$B_2O_3$=26.0 wt %
$ZnO$=1.0 wt %
$Na_2O$=2.5 wt %
$K_2O$=10.0 wt %
$TiO_2$=2.5 wt %
$ZrO_2$=1.0 wt %.

2. The implantable medical device of claim 1, wherein the feedthrough further includes a ceramic body covering the insulator body and surrounding the pins.

3. In an implantable medical device comprising a hermetically sealed case and a feedthrough hermetically sealed in an aperture of the case, wherein the improvement comprises:

the feedthrough comprising a ferrule of biocompatible, corrosion resistant metal selected from the group consisting of titanium, titanium alloys and niobium/titanium alloys, an insulator body sealed to the ferrule, wherein the insulator body comprises;
a glass having a nominal composition of about
$SiO_2$=52.0 wt %
$Al_2O_3$=5.0 wt %
$B_2O_3$=26.0 wt %
$ZnO$=1.0 wt %
$Na_2O$=2.5 wt %
$K_2O$=10.0 wt %
$TiO_2$=2.5 wt %
$ZrO_2$=1.0 wt %, and at least two pins of biocompatible, corrosion resistant metal in sealing engagement with the insulator body, the pins comprising a metal selected from the group consisting of tantalum, niobium, niobium/titanium alloys, platinum, platinum alloys, titanium, and titanium alloys.

4. The implantable medical device of claim 3, wherein the feedthrough includes three or more pins arranged in a linear array.

5. The implantable medical device of claim 3, wherein the insulator body is a single common body surrounding all of the pins.

6. The implantable medical device of claim 5, wherein the feedthrough further includes a ceramic body covering the insulator body and surrounding the pins.

7. The implantable medical device of claim 3, wherein the insulator body is a plurality of discrete bodies, each of the discrete bodies surrounding one of the pins.

8. The implantable medical device of claim 7, wherein the feedthrough includes a plurality of ceramic bodies, each of the ceramic bodies covering one of the discrete insulator bodies and surrounding one of the pins.

9. A multi-pin configured feedthrough comprising a ferrule comprising a biocompatible, corrosion resistant metal selected from the group consisting of titanium, titanium alloys and niobium/titanium alloys, an insulator body comprising:
a glass insulator body having a nominal composition of about:
$SiO_2$=52.0 wt %
$Al_2O_3$=5.0 wt %
$B_2O_3$=26.0 wt %
$ZnO$=1.0 wt %
$Na_2O$=2.5 wt %
$K_2O$=10.0 wt %
$TiO_2$=2.5 wt %
$ZrO_2$=1.0 wt %, and at least two pins comprising tantalum.

10. The feedthrough of claim 9, wherein the insulator body is a single common body surrounding all of the pins.

11. The feedthrough of claim 9, wherein the insulator body comprises a plurality of discrete bodies, each of the discrete bodies surrounding one of the pins.

12. The feedthrough of claim 9, further comprising at least one ceramic element overlying the insulator body.

13. The feedthrough of claim 9, wherein the feedthrough includes three or more pins arranged in a linear array.

14. An implantable pulse generator comprising a multi-pin configured feedthrough having a ferrule comprising a biocompatible, corrosion resistant metal selected from the group consisting of titanium, titanium alloys and niobium/titanium alloys, an insulator body comprising:
a glass insulator body having a nominal composition of about:
$Sio_2$=52.0 wt %
$Al_2O_3$=5.0 wt %
$B_2O_3$=26.0 wt %
$ZnO$=1.0 wt %
$Na_2O$=2.5 wt %
$K_2O$=10.0 wt %
$TiO_2$=2.5 wt %
$ZrO_2$=1.0 wt %, and at least two pins comprising tantalum.

* * * * *

UNITED STATES PATENT AND TRADEMARK OFFICE
CERTIFICATE OF CORRECTION

PATENT NO. : 5,817,984
DATED : Oct. 6, 1998
INVENTOR(S) : William J. Taylor et al.

It is certified that error appears in the above-identified patent and that said Letters Patent is hereby corrected as shown below:

On the title page:
 add item: "[73] Assignee: Medtronic, Inc., Minneapolis, Minn."

Signed and Sealed this

Twenty-ninth Day of August, 2000

Attest:

Q. TODD DICKINSON

*Attesting Officer*      *Director of Patents and Trademarks*